United States Patent
Sgroi

(10) Patent No.: US 10,206,679 B2
(45) Date of Patent: Feb. 19, 2019

(54) CURVILINEAR SURGICAL STAPLES

(71) Applicant: Covidien LP, Mansfield, MA (US)

(72) Inventor: Anthony Sgroi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 480 days.

(21) Appl. No.: 14/994,370

(22) Filed: Jan. 13, 2016

(65) Prior Publication Data
US 2017/0196564 A1    Jul. 13, 2017

(51) Int. Cl.
*A61B 17/064*    (2006.01)
*A61B 17/10*    (2006.01)
*A61B 17/068*    (2006.01)
*A61B 17/072*    (2006.01)
*A61B 17/04*    (2006.01)

(52) U.S. Cl.
CPC ............ *A61B 17/105* (2013.01); *A61B 17/04* (2013.01); *A61B 17/068* (2013.01); *A61B 17/0644* (2013.01); *A61B 17/07207* (2013.01); *A61B 2017/07214* (2013.01); *A61B 2017/07264* (2013.01)

(58) Field of Classification Search
CPC . A61B 17/068; A61B 17/0686; A61B 17/072; A61B 17/07207; A61B 17/07278; A61B 17/115; A61B 17/1155; A61B 17/064; A61B 17/0643; A61B 17/0644; A61B 2017/07214; A61B 2017/07264; A61B 2017/07271; A61B 2017/072282
USPC .. 227/19, 175.1, 176.1, 175.2, 178.1, 180.1, 227/902; 606/139, 143, 151, 153, 213, 606/219; 411/457, 472
See application file for complete search history.

(56) References Cited

U.S. PATENT DOCUMENTS

| | | |
|---|---|---|
| 4,261,244 A | 4/1981 | Becht et al. |
| 4,607,638 A * | 8/1986 | Crainich ............. F16B 15/0015 411/472 |
| 5,222,975 A | 6/1993 | Crainich |
| 5,350,400 A | 9/1994 | Esposito et al. |
| 5,653,372 A | 8/1997 | Richardson et al. |
| 5,667,527 A | 9/1997 | Cook |

(Continued)

FOREIGN PATENT DOCUMENTS

EP    2446838 A2    5/2012

OTHER PUBLICATIONS

European Examination Report dated Mar. 21, 2018 issued in corresponding EP Appln. No. 17151209.8.
European Search Report dated May 23, 2017 issued in corresponding European Application No. 17151209.8.

*Primary Examiner* — Scott A. Smith

(57) ABSTRACT

A surgical staple includes a backspan and a pair of deformable legs extending from the backspan and terminating in a penetrating end. The backspan and deformable legs are formed from a wire having a curvilinear cross-section defining a major axis and a minor axis with a portion of the wire above the major axis defining a first curved surface and a portion of the wire below the major axis defining a second curved surface, and a portion of the wire to the left of the minor axis defining a third curved surface and a portion to the right of the minor axis defining a fourth curved surface being different than the first, second, and third curved surfaces. One or more of the curved surfaces is different than the remaining curved surfaces.

12 Claims, 13 Drawing Sheets

(56) References Cited

U.S. PATENT DOCUMENTS

| | | | | |
|---|---|---|---|---|
| 6,149,660 A | * | 11/2000 | Laufer | A61B 17/0684 227/175.1 |
| 6,348,054 B1 | * | 2/2002 | Allen | A61B 17/0642 606/75 |
| 7,398,907 B2 | * | 7/2008 | Racenet | A61B 17/0644 227/176.1 |
| 7,735,703 B2 | * | 6/2010 | Morgan | A61B 17/105 227/176.1 |
| 7,824,426 B2 | | 11/2010 | Racenet et al. | |
| 7,926,691 B2 | * | 4/2011 | Viola | A61B 17/0644 227/175.1 |
| 8,186,556 B2 | * | 5/2012 | Viola | A61B 17/0644 227/177.1 |
| 8,220,690 B2 | * | 7/2012 | Hess | A61B 17/0644 227/181.1 |
| 8,590,762 B2 | * | 11/2013 | Hess | A61B 17/07207 227/175.1 |
| 8,672,208 B2 | | 3/2014 | Hess et al. | |
| 8,684,249 B2 | | 4/2014 | Racenet et al. | |
| 2004/0247415 A1 | * | 12/2004 | Mangone, Jr. | F16B 15/0015 411/457 |
| 2006/0015144 A1 | | 1/2006 | Burbank et al. | |
| 2008/0078800 A1 | * | 4/2008 | Hess | A61B 17/0644 227/175.1 |
| 2012/0109158 A1 | * | 5/2012 | Zammataro | A61B 17/122 606/142 |
| 2012/0241504 A1 | | 9/2012 | Soltz et al. | |
| 2013/0138125 A1 | | 5/2013 | Gonzales et al. | |

* cited by examiner

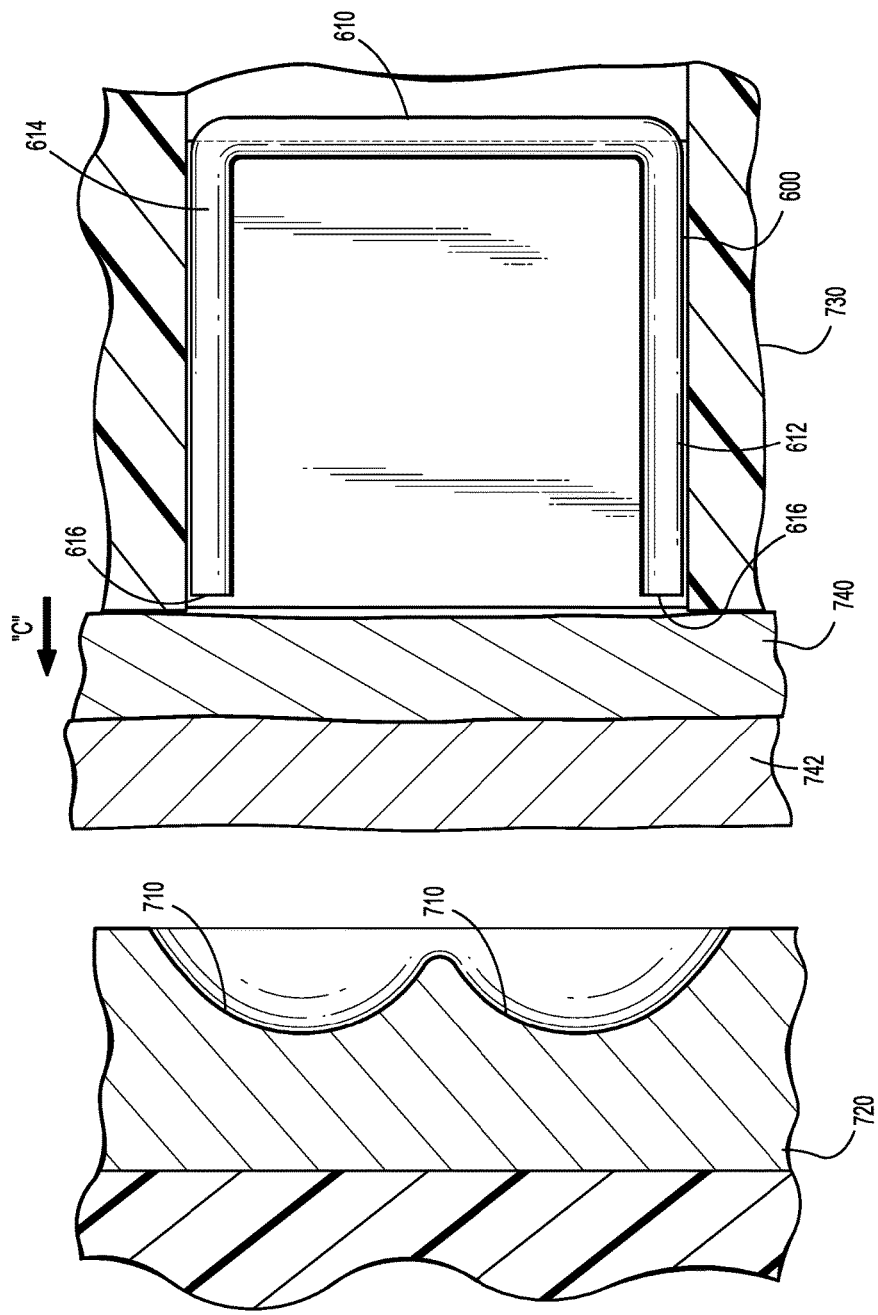

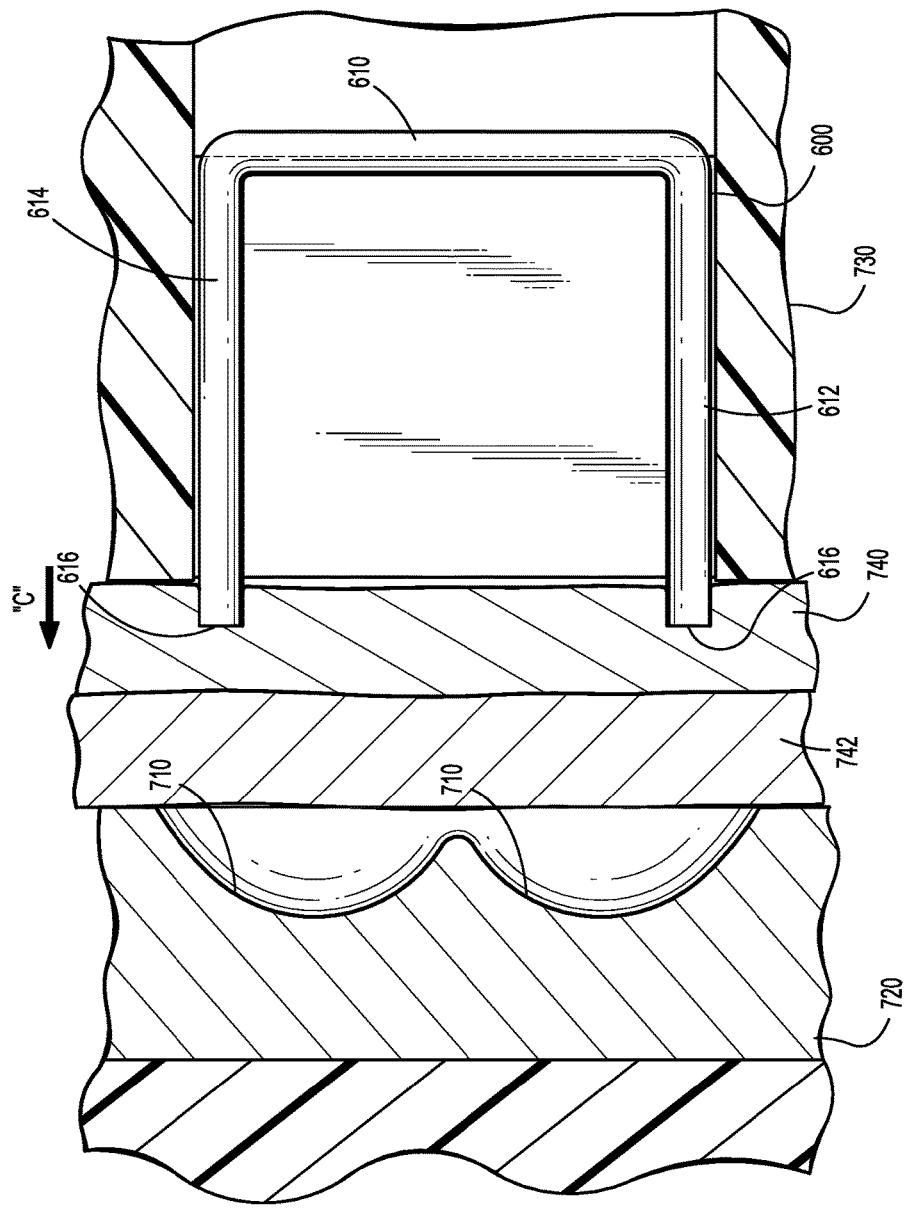

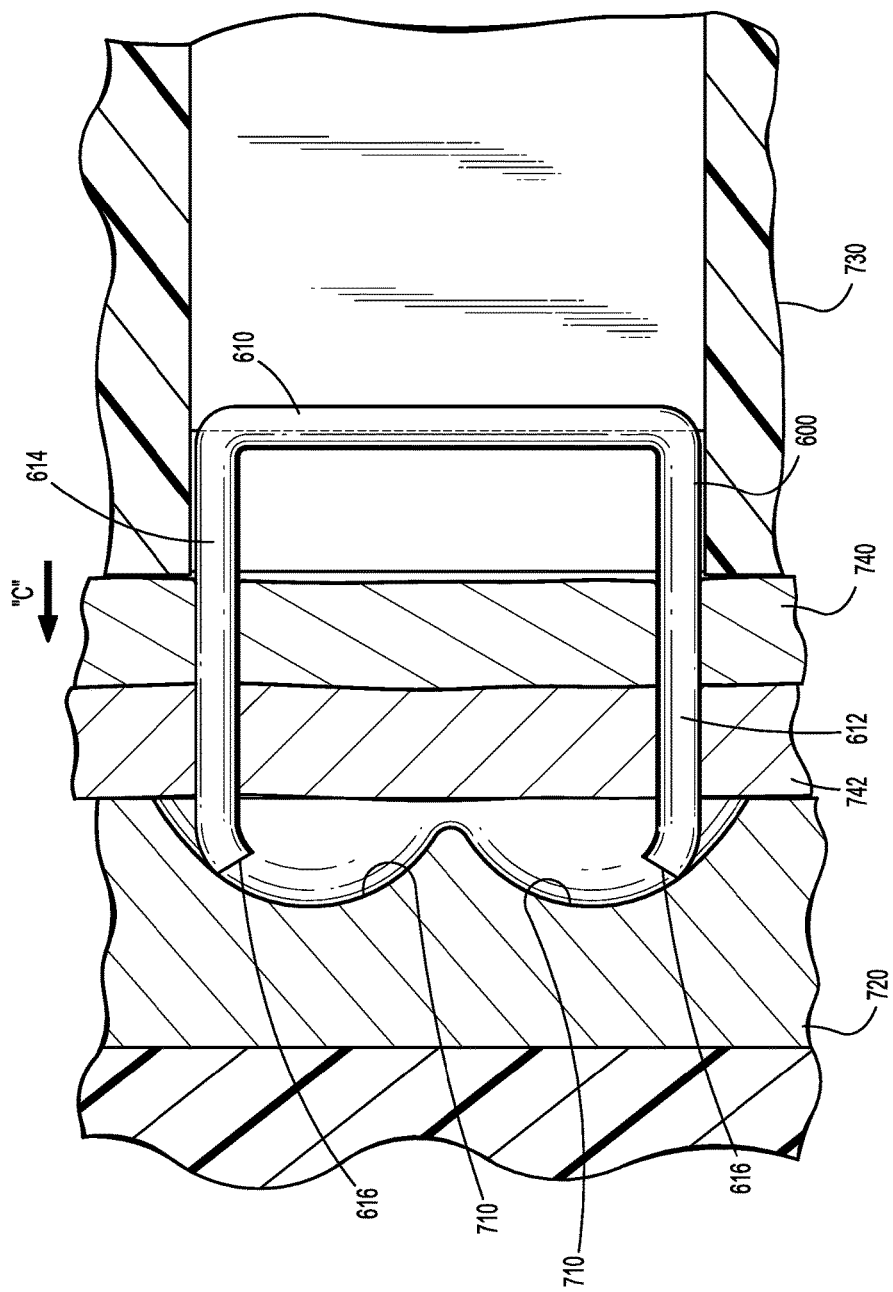

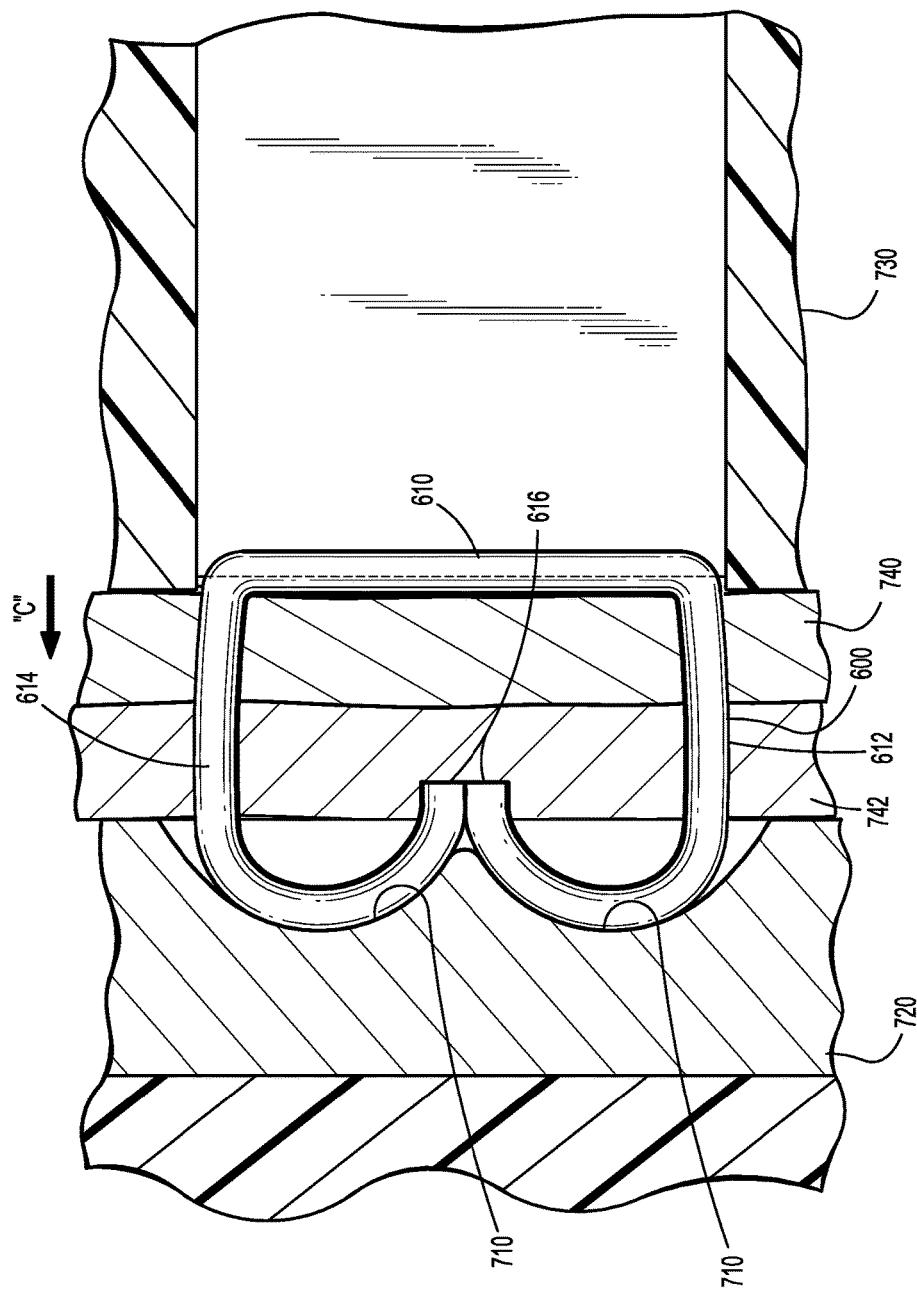

CURVILINEAR SURGICAL STAPLES

TECHNICAL FIELD

The present disclosure relates to medical instrumentation. More particularly, the present disclosure relates to surgical staples used with medical instrumentation.

BACKGROUND OF RELATED ART

Surgical stapling instruments are used in many life-saving surgical procedures. Surgical staples are usually mechanically inserted into tissue using surgical stapling instruments. In such devices, the staples are loaded into a cartridge in one or more elongated rows. A mechanism for pushing, or driving the stapler is actuated to drive the staples through two or more sections of tissue toward a deforming anvil. At the conclusion of the driving operation, the legs of each staple are clamped or bent, by the anvil, to a closed configuration to complete the suture and join the tissue sections together. Some surgical stapling devices drive and bend the staples aligned in a row sequentially in rapid sequence, while transverse surgical stapling devices drive and bend all staples simultaneously.

Known staple legs usually have a generally circular or rectangular configuration. However, the sharp transitions of the near square corners, where the staple penetrates tissue, may cause a leak path at the corners. Thus, the square corners do not allow for substantially equal pressure against all portions of the staple wire cross-section.

Thus, it would be desirable to provide a staple configuration for a staple designed to penetrate tissue and contact an anvil pocket on the opposing side of tissue, which, in complement with conventional cartridge and anvil technology, enhances correct staple formation while reducing leakage or tearing caused by sharp edges or corners at the distal end of the legs of staples.

SUMMARY

The present disclosure relates to a surgical staple. The surgical staple includes a backspan and a pair of deformable legs extending from the backspan and terminating in a leading penetrating end. The backspan and deformable legs are formed from a wire having a curvilinear cross-section defining a major axis and a minor axis with a portion of the wire above the major axis defining a first curved surface and a portion of the wire below the major axis defining a second curved surface, and a portion of the wire to the left of the minor axis defining a third curved surface and a portion to the right of the minor axis defining a fourth curved surface being different than the first, second, and third curved surfaces. One or more of the curved surfaces is different than the remaining curved surfaces.

In disclosed embodiments, the second curved surface is a mirror image of the first curved surface.

In disclosed embodiments, the fourth curved surface is different than the first, second, and third curved surfaces.

In disclosed embodiments, the first curved surface defines a first radius of curvature, the second curved surface defines a second radius of curvature, the third curved surface defines a third radius of curvature, and the fourth curved surface defines a fourth radius of curvature.

In disclosed embodiments, the fourth radius of curvature is greater than the third radius of curvature.

In disclosed embodiments, the first radius of curvature is equal to the second radius of curvature.

In disclosed embodiments, the first radius of curvature is greater than the third radius of curvature.

In disclosed embodiments, the first radius of curvature is greater than the fourth radius of curvature.

In disclosed embodiments, the first, second, third, and fourth curved surfaces apply about the same pressure against the surgical staple during tissue penetration.

The present disclosure relates to a cartridge for use with a surgical stapler, the cartridge having a plurality of individual directionally biased surgical staples therein and associated pushers for ejecting the staples from the cartridge, each of the staples being supported within the cartridge in spaced relation from adjacent staples. Each of the staples includes a backspan and a pair of deformable legs extending from the backspan and terminating in a leading penetrating end. The backspan and deformable legs are formed from a wire having a curvilinear cross-section defining a major axis and a minor axis with a portion of the wire above the major axis defining a first curved surface and a portion of the wire below the major axis defining a second curved surface, and a portion of the wire to the left of the minor axis defining a third curved surface and a portion to the right of the minor axis defining a fourth curved surface being different than the first, second, and third curved surfaces. One or more of the curved surfaces is different than the remaining curved surfaces.

The present disclosure relates to a cartridge including a plurality of individual surgical staples, each surgical staple having a pair of deformable legs and being deformable by contact of the legs with anvil pockets of an anvil, each of the staples being supported in spaced relation from adjacent staples within the cartridge. Each of the staples includes a backspan and a pair of deformable legs extending from the backspan and terminating in a leading penetrating end. The backspan and deformable legs are formed from a wire having a curvilinear cross-section defining a major axis and a minor axis with a portion of the wire above the major axis defining a first curved surface and a portion of the wire below the major axis defining a second curved surface, and a portion of the wire to the left of the minor axis defining a third curved surface and a portion to the right of the minor axis defining a fourth curved surface being different than the first, second, and third curved surfaces. One or more of the curved surfaces is different than the remaining curved surfaces.

DESCRIPTION OF THE DRAWINGS

The above and other aspects, features, and advantages of the present disclosure will become more apparent in light of the following detailed description when taken in conjunction with the accompanying drawings in which:

FIGS. 7A-7E illustrate the curvilinear staple of FIG. 6A fired into tissue, in accordance with the embodiments of the present disclosure;

DETAILED DESCRIPTION

Figure 1A:
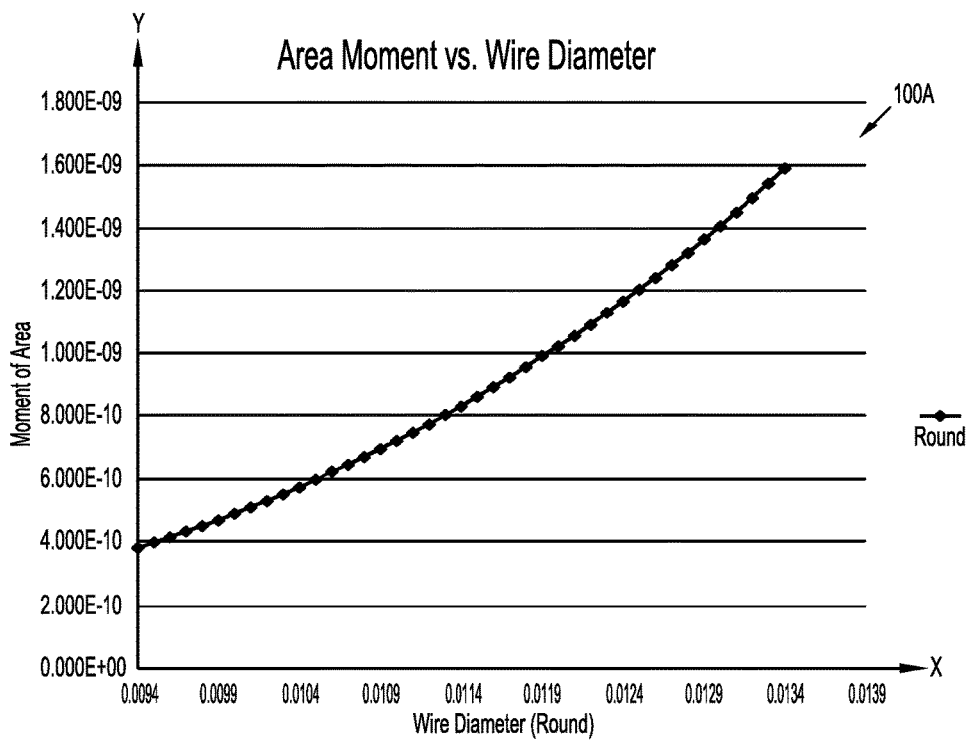
FIG. 1A illustrates a graph of a relationship of moment of areas vs. wire diameter for round wire cross-sections.

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user. In addition, the term "endoscopic" is used generally to refer to endoscopic, laparoscopic, or arthroscopic apparatus or procedures as well as any other surgical apparatus or procedure that is configured to extend or be performed through a small incision or a cannula inserted into a patient's body. Finally, the term "clinician" is used generally to refer to medical personnel including doctors, nurses, and support personnel.

Reference will now be made in detail to embodiments of the present disclosure. While certain exemplary embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Figure 1B:
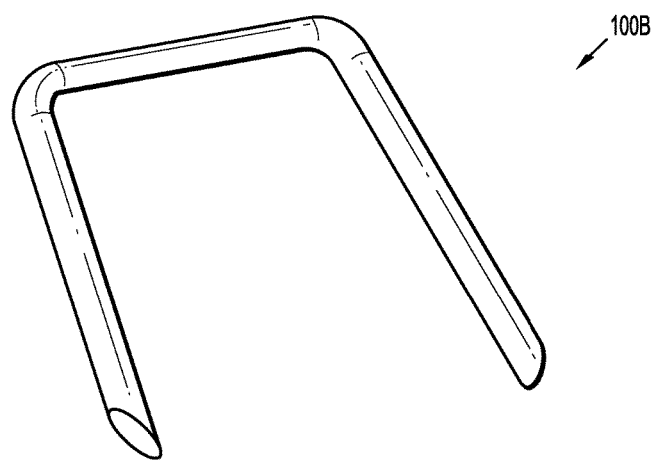
FIG. 1B illustrates an isometric view of a staple having a generally round or circular cross-section.

FIG. 1A illustrates a graph 100A of a relationship of moment of areas vs. wire diameter for round wire cross-sections, whereas FIG. 1B illustrates an isometric view 100B of a staple having a generally round or circular cross-section.

The surgical joining of tissue using stapling devices is known. In some instances, round or circular staple wire is used to create staples. Staples are typically created by use of round titanium wire. The round wire is obtained in spools and fed through various operations to ultimately cut, form, and sharpen the free-ends to form staples. The staples are assembled into an apparatus (see, e.g., FIGS. 7A-8C described below) to penetrate tissue for performing a joining procedure of tissue using a crimping operation of staples. However, the use of round or circular wire has some drawbacks, as illustrated in graph 100A of FIG. 1A where the x-axis represents the round wire diameter and the y-axis represents the moment of area.

For example, when encountering tough and fibrous tissue, the round or circular staple may be prematurely bent during the stapling process. Such bending may cause the staple ends to miss the receiving portion of the staple bucket. This may cause poorly formed staples which could form inferior retention of the tissue edges. Since the wire is round or circular, the resistance to bending is the same and bending may occur in any random direction.

One possible solution is to utilize larger diameter wire to increase stiffness. A higher stiffness due to a larger diameter would produce a relatively higher moment of area across the cross section. As seen in FIG. 1A, the moment of area rises with a corresponding rise in wire diameter. Thus, by selecting larger diameter staple wire, a stiffer wire may be utilized to resist unintentional bending when being forced through tough tissue. However, a stiffer wire would increase the difficulty of forming the staple during the forming process.

Figure 2:
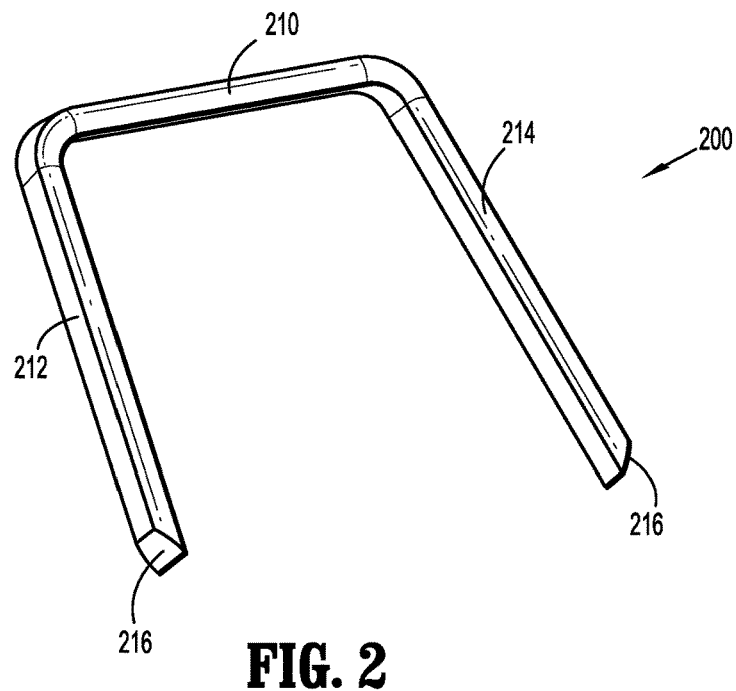
FIG. 2 illustrates an isometric view of a staple having a generally rectangular cross-section.

FIG. 2 illustrates an isometric view of a staple 200 having a generally rectangular cross-section.

Figure 3:
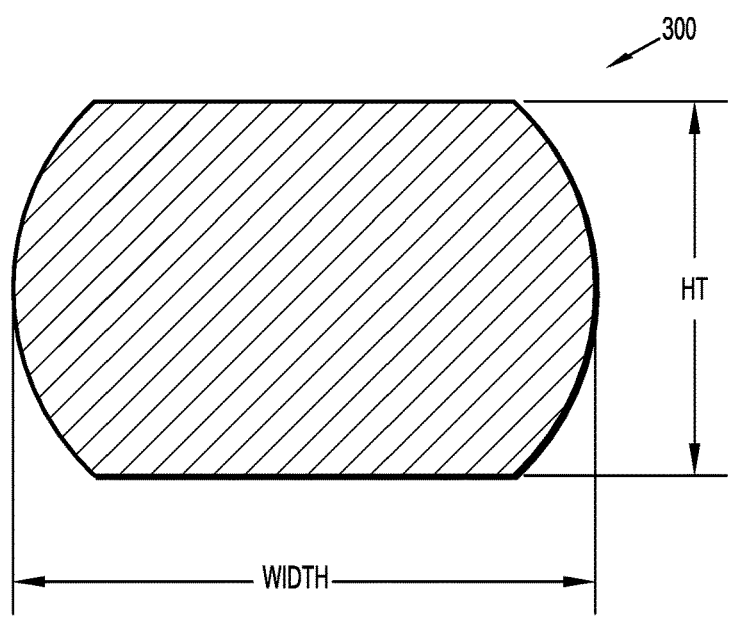
FIG. 3 illustrates a cross-section of the staple of FIG. 2.

The staple 200 includes a backspan 210 and a pair of deformable legs 212, 214 extending from the backspan 210. The pair of deformable legs 212, 214 terminates with a penetrating structure 216. FIG. 3 illustrates a cross-section 300 of the staple 200 of FIG. 2. The staple cross-section 300 has a width that is greater than the height, HT. Thus, the stiffness when trying to bend about the wider width is higher than the stiffness when attempting to bend about the smaller thickness. This depends on the differences of moment of areas for a constant material property. Therefore, it is advantageous to allow for the formation of staples using the lower stiffness wire orientation. This allows staples to be formed within an acceptable force value along the formation direction.

However, the use of a generally rectangular staple may possess a disadvantage. In particular, the use of a generally rectangular staple across a staple line does provide lower burst resistance in tissue as compared to a round staple. When a staple pierces through tissue, a round staple tends to have a lower leak path as compared to a rectangular staple. The round cross-section may provide uniform pressure along the piercing surface as compared to pointy edges of the rectangular cross-section.

Therefore, the round or circular staple of FIG. 1B, as well as the rectangular staple of FIG. 2, when encountering tough and fibrous tissue, may be prematurely bent during the stapling process. Such bending may cause such staple ends to miss the receiving portion of the staple bucket. This may cause poorly formed staples which could form inferior retention of the tissue edges. Instead, an elliptical staple configuration (see FIG. 4) or an oval staple configuration (see FIG. 5) or a curvilinear staple configuration (see FIG. 6B) may provide for application of more uniform pressure against the surgical staple after tissue penetration (see FIGS. 7A-7E described below). The uniform pressure results in reduced likelihood of leak paths or tears at the point of contact between the penetrating ends and first and second tissue layers (see FIGS. 7A-7E described below).

Figure 4:
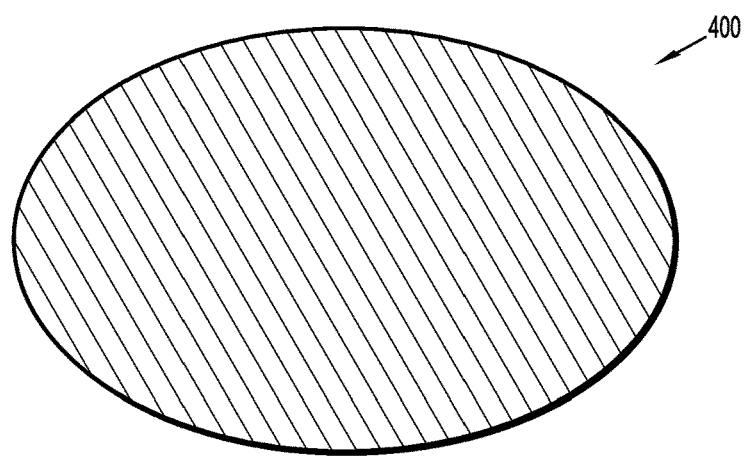
FIG. 4 illustrates an elliptical cross-section of a staple, in accordance with the embodiments of the present disclosure.
Figure 5:
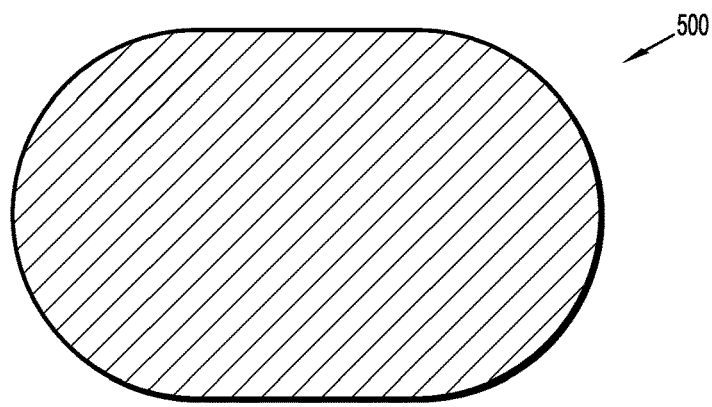
FIG. 5 illustrates an oval cross-section of a staple, in accordance with the embodiments of the present disclosure.

FIG. 4 illustrates an elliptical cross-section 400 of a staple, in accordance with the embodiments of the present disclosure, whereas FIG. 5 illustrates an oval cross-section 500 of a staple, in accordance with the embodiments of the present disclosure.

The staple 400 of FIG. 4 has a uniform curvature along its entire perimeter coupled with a width that is greater than its height.

The staple 500 of FIG. 5 has opposing flats with a tangent radius terminating along each end. Thus, there exists a smooth transition of the flats to the curvature when the width is greater than the height regarding the staple wire cross-section.

Figure 6A:
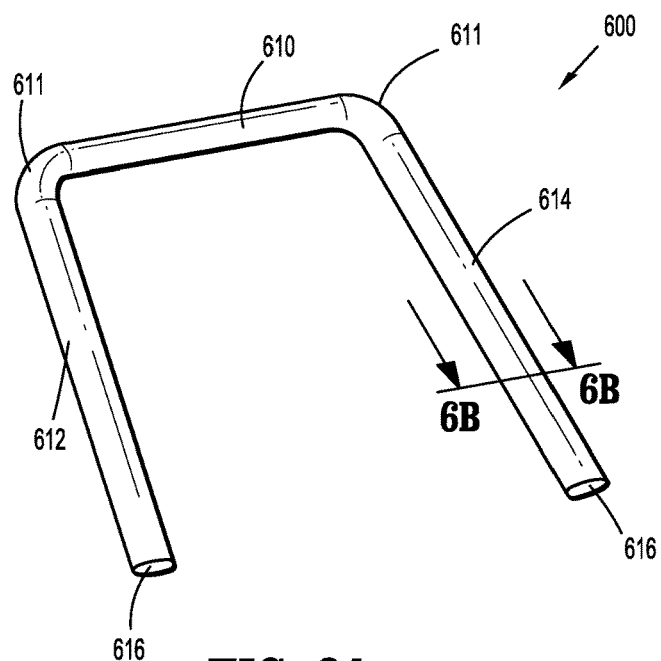
FIG. 6A illustrates an isometric view of a curvilinear staple, in accordance with the embodiments of the present disclosure.

FIG. 6A illustrates an isometric view of staple 600 having a curvilinear cross-section, in accordance with the embodiments of the present disclosure.

The staple 600 includes a backspan 610 and a pair of deformable legs 612, 614 extending from curved regions 611 of the backspan 610. The pair of deformable legs 612, 614 terminates with penetrating structures 616. Each deformable leg 612, 614 has a curvilinear cross-section bounded by first, second, third, and fourth outer curved surfaces 660, 670, 680, 690, as shown in FIG. 6B, described below.

Figure 6B:
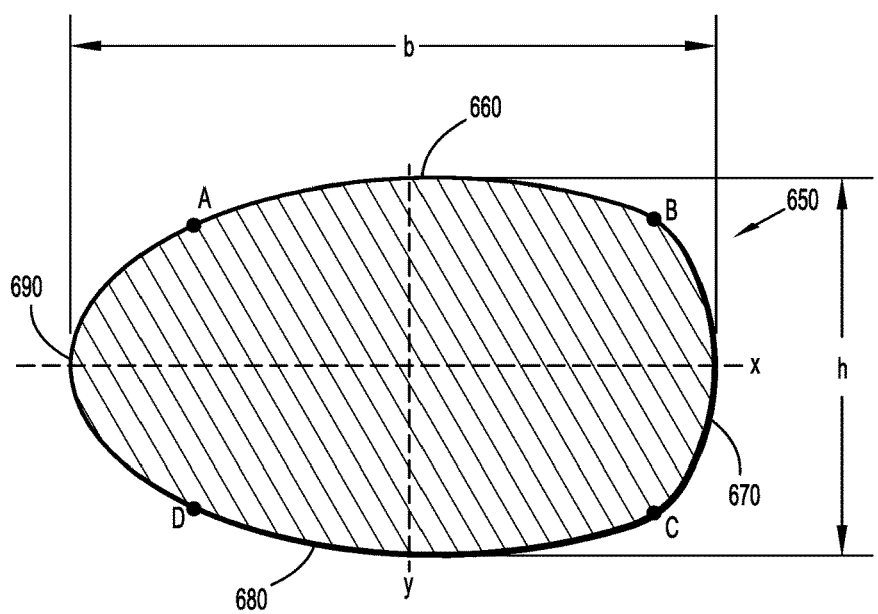
FIG. 6B illustrates a curvilinear cross-section of the staple of FIG. 6A, in accordance with the embodiments of the present disclosure.

FIG. 6B illustrates a curvilinear cross-section 650 of the staple 600, in accordance with the embodiments of the present disclosure.

The curvilinear cross-section 650 has a first surface 660, a second surface 670, a third surface 680, and a fourth surface 690. The first, second, third, and fourth surfaces 660, 670, 680, and 690 are rounded surfaces. The first, second, third, and fourth surfaces 660, 670, 680, and 690 may also be referred to as being arched or bowed or curved or convex surfaces. The first surface 660 is defined between points A and B, the second surface 670 is defined between points B and C, the third surface 680 is defined between points C and D, and the fourth surface 690 is defined between points D and A.

The first surface 660 thus has a first curvature, the second surface 670 has a second curvature, the third surface 680 has a third curvature, and the fourth surface 690 has a fourth curvature. The first surface 660 is in diametrically opposed relation to the third surface 680, whereas the second surface 670 is in diametrically opposed relation to the fourth surface 690. The first curvature may be substantially equal or the same with the third curvature. The fourth curvature may be greater than the second curvature. Additionally, the first and third curvatures may be greater than the second and fourth curvatures. Additionally, each of the first, second, third, and fourth surfaces 660, 670, 680, 690 may be the same along the entire length of the pair of deformable legs 612, 614. However, one skilled in the art may contemplate that the first, second, third, and fourth surfaces 660, 670, 680, 690 may be different along the length of the pair of deformable legs 612, 614. For example, the first surface 660 may have a first radius of curvature along a first length and a second radius of curvature along a second length. The second, third, and fourth surfaces 670, 680, 690 may also be defined in a similar manner.

In this embodiment, the cross section is formed in a substantially curvilinear configuration, as shown in FIG. 6B, with "x" designating the major base dimension (b) and "y" designating the minor height dimension (h) of the crown portion of the curvilinear staple 600 when positioned in an inverted-U configuration, as shown in FIG. 6A. As used herein, the curvilinear staple 600 is intended to be formed about the x dimension (x axis). Thus, as illustrated in FIGS. 7A-7E, staple 600 is formed downward relative to the page.

This cross-sectional configuration may be achieved by any known method including extrusion, rolling, coining, etc. Preferably, this configuration is accomplished by flat rolling round wire stock on opposing sides. In the fabrication process, the stock can be pre-rolled by the wire manufacturer or may be round wire stock which is rolled into the desired cross-sectional configuration by the staple manufacturer.

The backspan 610 and deformable legs 612, 614 are formed from a wire having a curvilinear cross-section defining a major axis "x" and a minor axis "y" with a portion of the wire above the major axis "x" defining a first curved surface 660 and a portion of the wire below the major axis "x" defining a third curved surface 680 that is a mirror image of the first curved surface 660, and a portion of the wire to the left of the minor axis "y" defining a second curved surface 670 and a portion to the right of the minor axis "y" defining a fourth curved surface 690 being different than the first, second, and third curved surfaces 660, 670, 680.

Figure 6C:
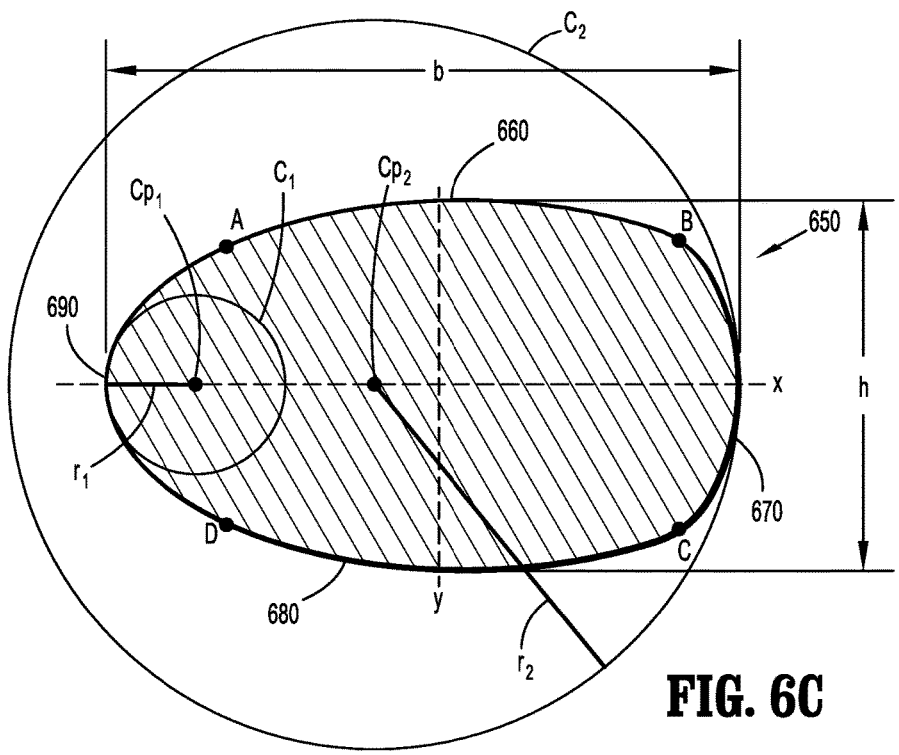
FIGS. 6C and 6D illustrate radius of curvature of different curved surfaces of the curvilinear staple of FIG. 6A, in accordance with the embodiments of the present disclosure.
Figure 6D:
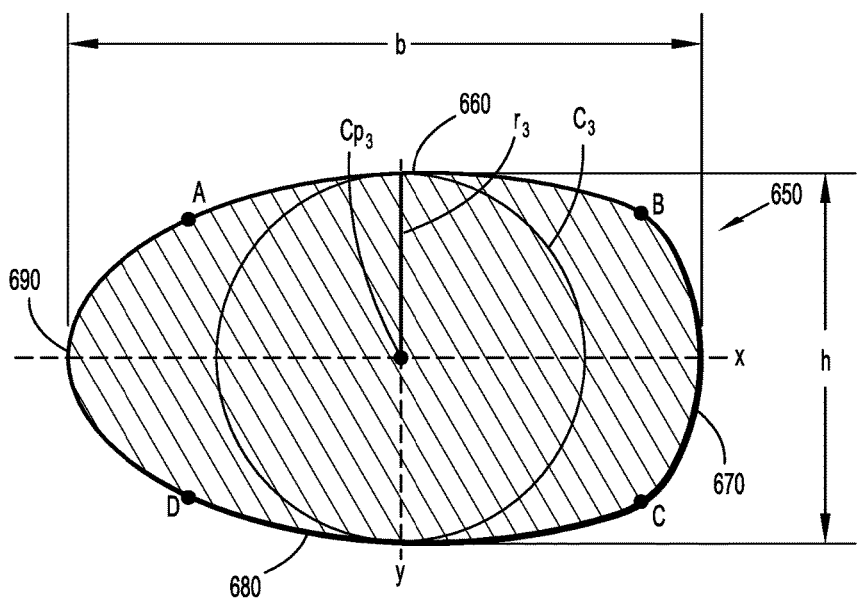

In FIGS. 6C and 6D, the radius of curvature is the radius of a circle that touches a curve at a given point and has the same tangent and curvature at that point. Thus, FIG. 6C, for example, illustrates the radius of curvature of the fourth surface 690 as $r_1$, a circle as $c_1$, and the center point $c_{p1}$ of the circle $c_1$. FIG. 6C also illustrates the radius of curvature of the second surface 670 as $r_2$, a circle as $c_2$, and the center point $c_{p2}$ of the circle $c_2$. The circle $c_2$ is larger than the circle $c_1$. Similarly, FIG. 6D illustrates the radius of curvature of the first surface 660 as $r_3$, a circle as $c_3$, and the center point $c_{p3}$ of the circle $c_3$. The radius of curvature of the first surface 660 is equal to the radius of curvature of the third surface 680. The circle $c_3$ is larger than the circle $c_1$, whereas the circle $c_2$ is larger than the circles $c_1$ and $c_3$. Stated differently, $c_2 > c_3 > c_1$.

With reference to FIGS. 6C and 6D, the first curved surface 660 defines a first radius of curvature $r_3$, the second curved surface 670 defines a second radius of curvature $r_2$, the third curved surface 680 defines a third radius of curvature $r_3$, and the fourth curved surface 690 defines a fourth radius of curvature $r_1$. The fourth radius of curvature $r_1$ is less than the second radius of curvature $r_2$, whereas the first radius of curvature $r_3$ is equal to the third radius of curvature $r_3$. Additionally, the first radius of curvature $r_3$ is less than the second radius of curvature $r_2$. Also, the first radius of curvature $r_3$ is greater than the fourth radius of curvature $r_1$. Stated differently, $r_2 > r_3 > r_1$.

In operation, since staples are forced through thick tissue and the staple cartridge and anvil can flex as tissue is compressed and can move slightly relative to another, this affects the point of contact between the staple leg points and the anvil. For example, if the anvil moves slightly out of alignment, the staple legs contact a different point of the anvil which can affect uniform formation of the staple. Additionally, due to manufacturing tolerances, the staple points may not contact the anvil in the exact optimal location. Although such staple formation is clinically satisfactory and effective, the curvilinear staple of the present application provides for more uniform formation of the rows of staples and accommodates for manufacturing tolerances as it is more resistant to twisting. That is, the curvilinear staple has the tendency to bend in the direction of the thinner dimension which is desired since in this case the thinner dimension defines the desired bending direction. By relaxing manufacturing tolerances, the cost of manufacturing is reduced as well.

Therefore, in summary, the curvilinear cross-section is defined by a plurality of surfaces, where the plurality of surfaces are connected to each other with rounded or arched or bowed or curved edges. An advantage of using a curvilinear cross-section for the backspan 610 and legs 612, 614 is that the rounded or curved edges of the curvilinear cross-section apply a uniform pressure against the surgical curvilinear staple 600 after tissue penetration (see FIGS. 7A-7E described below). The uniform pressure results in reduced likelihood of leak paths or tears at the point of contact between the penetrating ends 616 and first and second tissue layers 740, 742 (see FIGS. 7A-7E described below).

FIGS. 7A-7E illustrate the curvilinear staple 600 of FIG. 6A fired into tissue, in accordance with the embodiments of the present disclosure.

FIG. 7A depicts the curvilinear staple 600 of FIG. 6A in staple cartridge 730. A pusher (see FIG. 7F) engages the backspan 610 of the curvilinear staple 600 to propel the tips 616 of the curvilinear staple 600 toward first tissue layer 740. In FIG. 7A, the tips 616 of the curvilinear staple 600 are positioned adjacent the first tissue layer 740.

FIG. 7B depicts the tips 616 of the curvilinear staple 600 penetrating the first tissue 740 layer for the first time.

FIG. 7C depicts the tips 616 of the curvilinear staple 600 engaging the pockets 710 of the anvil 720. The tips 616 of the curvilinear staple 600 start to bend and assume the shape of the pockets 710. The curvilinear staple 600 has penetrated the first tissue layer 740 and the second tissue layer 742.

Figure 7D:
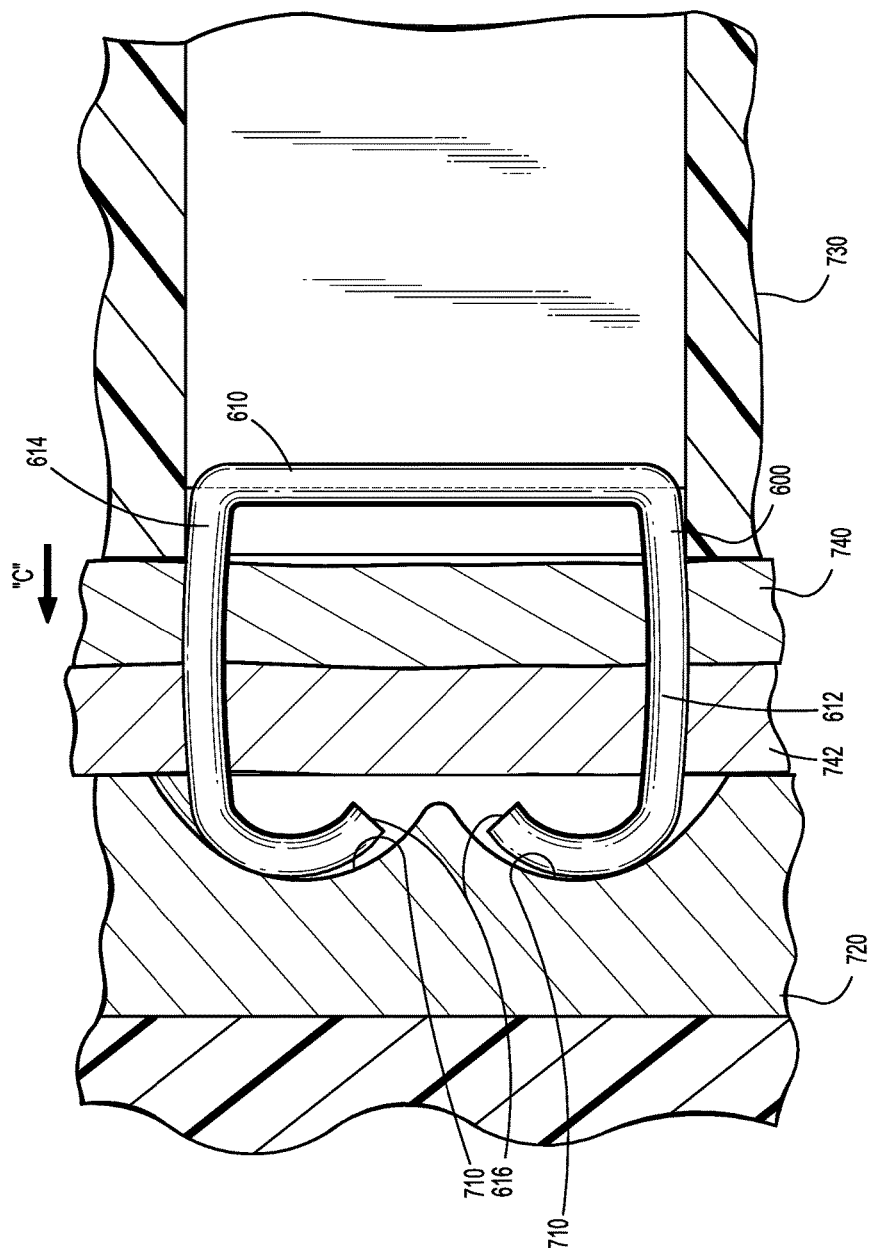

FIG. 7D depicts the tips 616 of the curvilinear staple 600 re-entering the second tissue layer 742 on the back-end, after the tips 616 of the curvilinear staple 600 assume the shape of the pockets 710.

FIG. 7E depicts the curvilinear staple 600 in its final state binding the tissue layers 740, 742.

FIGS. 7A-7E illustrate that by using staple 600 having deformable legs 612, 614 with a curvilinear cross-section, that such staple configuration allows for easier bending in the staple formation direction and the constant curvature of the curvilinear cross-section allows for more uniform pressure against the staple 600 after piercing the first and second tissue layers 740, 742 to reduce potential tearing or leak paths at the penetration points. This is further evident with reference to FIGS. 8A-8C described below.

Figure 7F:
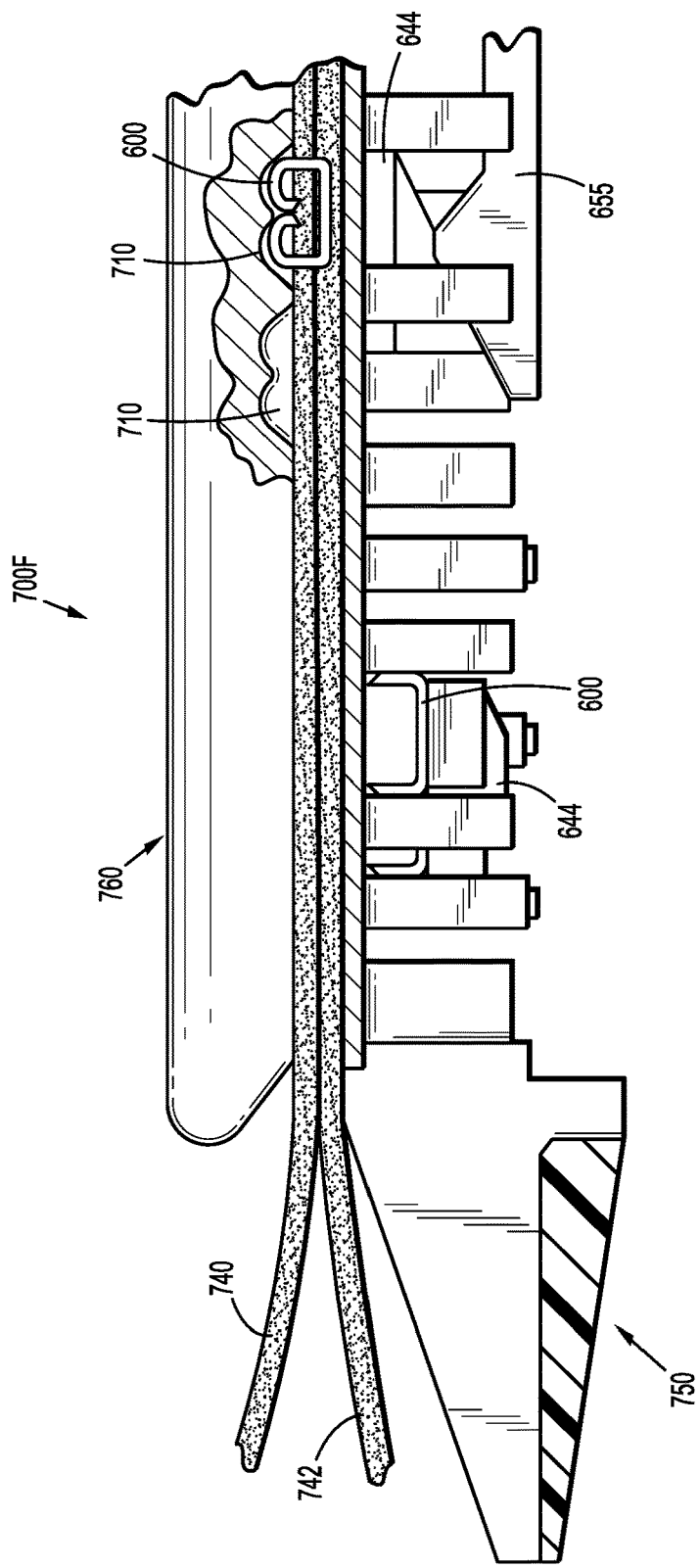
FIG. 7F illustrates a side view in partial cross-section of a staple cartridge and anvil, in accordance with the embodiments of the present disclosure.

FIG. 7F illustrates a side view 700F in partial cross section of a staple cartridge 750 and anvil 760, in accordance with an embodiment of the present disclosure.

With reference to FIG. 7F, an embodiment of staple cartridge 750 of the present disclosure includes pusher elements or staple drivers 644, and surgical fasteners or curvilinear staples 600. The curvilinear staples 600 and staple drivers 644 are disposed such that as cam bars 655 move distally and longitudinally through staple cartridge 750, staple drivers 644 drive curvilinear staples 600 through body tissue layers 740 and 742 which are to be joined, and against anvil 760 where the legs of the curvilinear staples 600 are crimped in pockets 710. An anvil including such a staple forming pocket is disclosed in U.S. Pat. No. 5,480,089, the entirety of which is incorporated herein by reference.

Figure 8A:
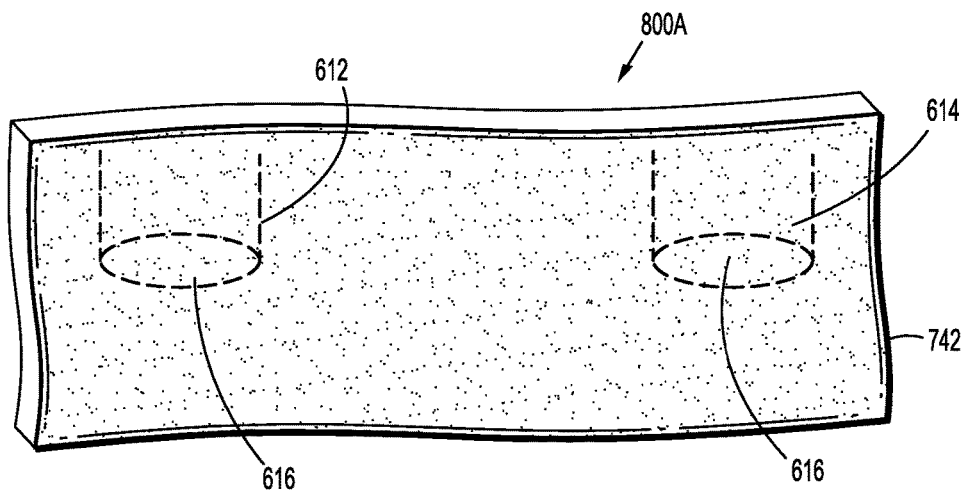
FIGS. 8A-8C illustrate the tips of the curvilinear staple of FIG. 6A penetrating tissue, in accordance with the embodiments of the present disclosure.
Figure 8B:
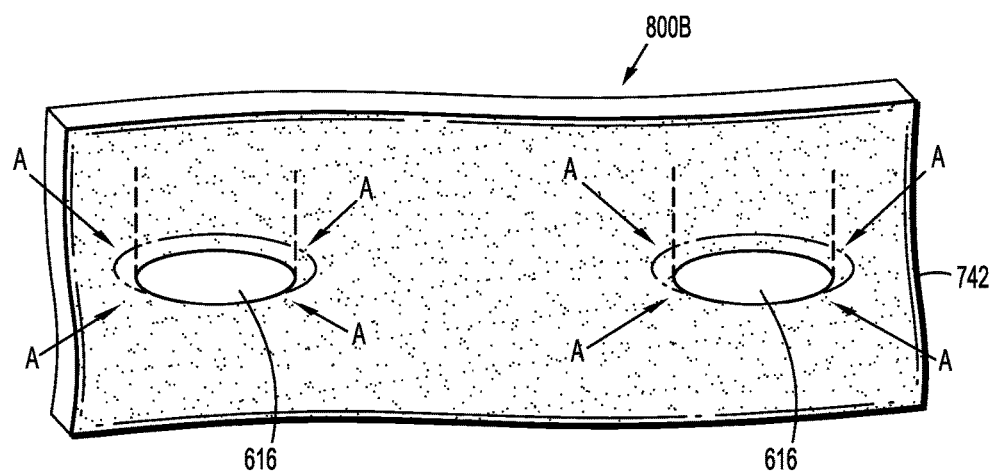
Figure 8C:
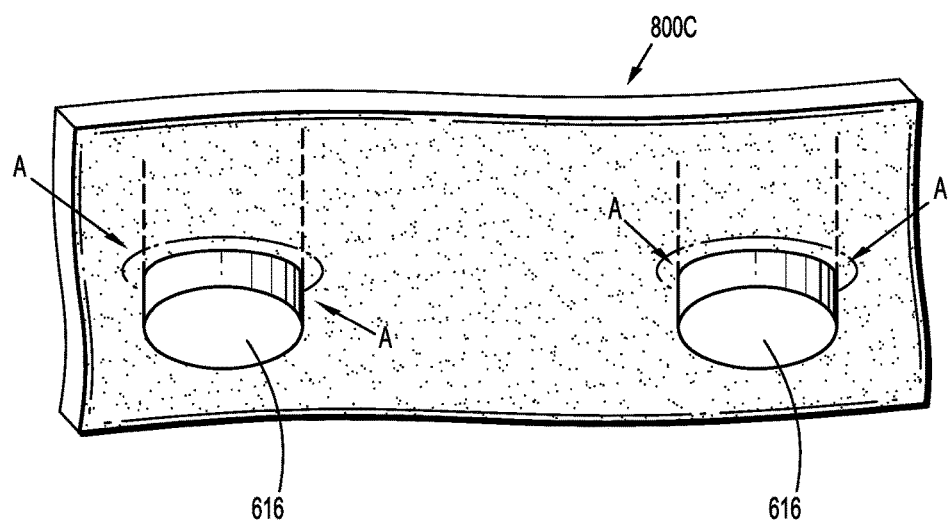

FIGS. 8A-8C illustrate the tips 616 of the curvilinear curvilinear staple 600 of FIG. 6A penetrating first tissue layer 740, in accordance with the embodiments of the present disclosure. For simplicity, only one layer of tissue is shown to illustrate the penetration. However, one skilled in the art may contemplate the penetration of one or more layers of tissue.

FIG. 8A depicts a first view 800A where the tips 616 of the curvilinear staple 600 approach the first tissue layer 740.

FIG. 8B depicts a second view 800B where the tips 616 of the curvilinear staple 600 are at the penetration points (areas or regions) "A" of the first tissue layer 740.

FIG. 8C depicts a third view 800C where the tips 616 of the curvilinear staple 600 are pierced through the penetration points (areas or regions) "A," such that the tips 616 of the curvilinear staple 600 extend through the first tissue layer 740.

It is noted that there is uniform pressure at the penetration points (areas or regions) "A" when the tips 616 of the curvilinear staple 600 pierce the first tissue layer 740, such that no tearing and no leaks occur at such penetration points (areas or regions) "A." Moreover, substantially equal pressure is applied to all portions around the edge or perimeter or circumference of the curvilinear cross-section of the curvilinear staple 600 resulting in reduced likelihood of leak paths or tears.

It is to be understood that the various embodiments shown and described herein are to be taken as exemplary. Elements and materials, and arrangements of those elements and materials, may be substituted for those illustrated and described herein, parts may be reversed, and certain features of the present disclosure may be utilized independently, all as would be apparent to one skilled in the art after having the benefit of the description herein. Changes may be made in the elements described herein without departing from the spirit and scope of the present disclosure and following claims, including their equivalents. It is to be understood that the particular examples and embodiments set forth herein are non-limiting, and modifications to structure, dimensions, materials, and methodologies may be made without departing from the scope of the present disclosure.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. A surgical staple comprising:
a backspan; and
a pair of deformable legs extending from the backspan and terminating in a penetrating end;
wherein the backspan and deformable legs are formed from a wire having a curvilinear cross-section defining a major axis and a minor axis with a portion of the wire above the major axis defining a first curved surface having a first radius of curvature and a portion of the wire below the major axis defining a second curved surface having a second radius of curvature, a portion of the wire to the left of the minor axis defining a third curved surface having a third radius of curvature and a portion to the right of the minor axis defining a fourth curved surface having a fourth radius of curvature; and
wherein the first and second curved surfaces are symmetric with respect to the major axis, the first radius of curvature being greater than the third radius of curvature, but less than the fourth radius of curvature.

2. The surgical staple according to claim 1, wherein the first, second, third, and fourth curved surfaces apply about the same pressure against the surgical staple during tissue penetration.

3. The surgical staple according to claim 1, wherein the first, second, third, and fourth curved surfaces have non-planar curvature.

4. The surgical staple according to claim 1, wherein the curvilinear cross-section has a length along the major axis and a width along the minor axis, the length greater than the width.

5. A cartridge for use with a surgical stapler, the cartridge having a plurality of individual directionally biased surgical staples therein and associated pushers for ejecting the staples from the cartridge, each of the staples being supported within the cartridge in spaced relation from adjacent staples and each of the staples comprising:
  a backspan; and
  a pair of deformable legs extending from the backspan and terminating in a penetrating end;
  wherein the backspan and deformable legs are formed from a wire having a curvilinear cross-section defining a major axis and a minor axis with a portion of the wire above the major axis defining a first curved surface having a first radius of curvature and a portion of the wire below the major axis defining a second curved surface having a second radius of curvature, a portion of the wire to the left of the minor axis defining a third curved surface having a third radius of curvature and a portion to the right of the minor axis defining a fourth curved surface having a fourth radius of curvature; and
  wherein the first or second radius of curvature is greater than the third radius of curvature, but less than the fourth radius of curvature.

6. The cartridge according to claim 5, wherein the second curved surface is a mirror image of the first curved surface.

7. The cartridge according to claim 6, wherein the fourth curved surface is different than the first, second, and third curved surfaces.

8. The cartridge according to claim 5, wherein the first radius of curvature is equal to the second radius of curvature.

9. The cartridge according to claim 5, wherein the first, second, third, and fourth curved surfaces apply about the same pressure against the surgical staple during tissue penetration.

10. A cartridge including a plurality of individual surgical staples, each surgical staple having a pair of deformable legs and being deformable by contact of the legs with anvil pockets of an anvil, each of the staples being supported in spaced relation from adjacent staples within the cartridge and comprising:
  a backspan; and
  a pair of deformable legs extending from the backspan and terminating in a penetrating end;
  wherein the backspan and deformable legs are formed from a wire having a curvilinear cross-section defining a major axis and a minor axis with a portion of the wire above the major axis defining a first curved surface having a first radius of curvature and a portion of the wire below the major axis defining a second curved surface having a second radius of curvature, a portion of the wire to the left of the minor axis defining a third curved surface having a third radius of curvature and a portion to the right of the minor axis defining a fourth curved surface having a fourth radius of curvature, the curvilinear cross-section having a length extending along the major axis and a width extending along the minor axis, the length greater than the width; and
  wherein the first or second radius of curvature is greater than the third radius of curvature, but less than the fourth radius of curvature.

11. The cartridge according to claim 10, wherein the second curved surface is a mirror image of the first curved surface; and wherein the fourth curved surface is different than the first, second, and third curved surfaces.

12. The cartridge according to claim 10, wherein the first, second, third, and fourth curved surfaces apply about the same pressure against the surgical staple during tissue penetration.

* * * * *